United States Patent [19]

Karwowski

[11] 4,216,526
[45] Aug. 5, 1980

[54] ORGANIZATION OF TOMOGRAPHIC DATA FOR A TWO DIMENSIONAL DISPLAY

[75] Inventor: Wieslaw A. Karwowski, Perivale, England

[73] Assignee: E M I Limited, Hayes, England

[21] Appl. No.: 869,471

[22] Filed: Jan. 16, 1978

[30] Foreign Application Priority Data

Feb. 2, 1977 [GB] United Kingdom ............. 4279/77

[51] Int. Cl.² ............................................. A61B 6/00
[52] U.S. Cl. ................................... 364/414; 364/515; 250/363 R; 250/445 R; 250/445 T
[58] Field of Search ............... 364/414, 582, 900, 515; 250/445 T, 445 R, 363 S, 363 R

[56] References Cited

U.S. PATENT DOCUMENTS

| | | | |
|---|---|---|---|
| 3,153,224 | 10/1964 | Taylor, Jr. | 364/731 |
| 3,499,146 | 3/1970 | Richards | 250/445 |
| 3,519,997 | 7/1970 | Bernhart et al. | 364/900 |
| 3,684,886 | 8/1972 | Muehllegner | 250/445 |
| 3,779,457 | 12/1973 | Cornyn, Jr. | 364/582 |
| 3,852,603 | 12/1974 | Muehllegner | 250/445 |
| 4,044,240 | 8/1977 | Cox, Jr. et al. | 364/414 |
| 4,048,501 | 9/1977 | Grenier | 364/414 |

Primary Examiner—Malcolm A. Morrison
Assistant Examiner—Gary Chin
Attorney, Agent, or Firm—Cooper, Dunham, Clark, Griffin & Moran

[57] ABSTRACT

Computerized tomographic (CT) apparatus provides data for cross-sectional slices in the body of a patient. In certain circumstances it is desirable to view the data as shadowgrams, that is conventional X-ray pictures giving sums of absorption as viewed in a selected direction. This invention provides shadowgram data from a plurality of CT pictures by effecting coordinate transformation and summation along appropriate lines. It is applicable to data for cross-sectional slices whether radiographic or otherwise.

12 Claims, 10 Drawing Figures

ORGANIZATION OF TOMOGRAPHIC DATA FOR A TWO DIMENSIONAL DISPLAY

The present invention relates to apparatus for displaying a representation of data representative of a quantity measured for a body under examination. The invention may be used, for example, with diagnostic X-ray apparatus of the type known as Computerized Axial Tomography (CAT) scanners.

Apparatus of that type, examples of which are described in British Pat. No. 1,283,915, used radiographic techniques to produce representations of the absorption of penetrating radiation in one or more cross-sections of the body of a patient. The absorption is represented by absorption coefficients of individual elements of a matrix of elements notionally delineated in each such cross-section.

In U.S. Pat. No. 4,029,948 there is described apparatus, for displaying such data, which can hold and display individually such representations for a plurality of such cross-sections, typically eight. That apparatus is also capable of interpolating between corresponding matrix elements of adjacent cross-sections to provide data representative of further cross-sections intermediate to those actually examined.

A further development of that display apparatus, described in U.S. Pat. No. 4,086,492, uses such interpolation to provide data representative of cross-sections, not actually examined, which are inclined to the examined cross-sections. Both of these arrangements include a store such as a disc store, holding the measured data and allowing the data to be derived for different cross-sections for combination as required.

In certain circumstances, however, it may be desired to display a "shadowgram" X-ray picture, i.e. a conventional form of X-ray picture showing in shadow form all parts of the body absorbing X-rays in a chosen direction of viewing.

It is an object of this invention to provide an arrangement capable of deriving shadowgram pictures at a desired orientation in the body.

According to the invention there is provided an apparatus for processing, for display, values of a quantity, for example X-ray absorption, measured in a region of the body of a patient. The apparatus includes storage means for receiving data signals representing the measured values for respective elemental areas of a plurality of cross-sectional slices of the body, each data signal being identified by the co-ordinates of the respective element in the body according to a first co-ordinate system. Transformation means are provided to transform the co-ordinates for the data signals to the co-ordinates for the same elements according to a second co-ordinate system. This second coordinate system is in two dimensions orthogonal to a selected direction in the body. Means are also provided for summing, for the plurality of slices, data signals which are identified by substantially the same co-ordinates in the second system, to provide a representation which is the sum of the individual slices viewed in the selected direction.

In order that the invention may be clearly understood and readily carried into effect an example thereof will now be described with reference to the accompanying drawings of which.

In principle a shadowgram is obtained by adding together the absorptions of all elements, for each of a number of lines passing in a chosen direction through the measured slices. The situation is illustrated in simplified form in FIG. 1. Five slices, representing the absorption for corresponding cross-sections of the body of a patient, are shown. These may be derived by any suitable CAT technique such as that of the said U.S. Pat. No. 3,778,614 or, for example, U.S. Pat. No. 4,035,647 both of which patents are incorporated herein by reference. In this simplified example each slice is considered to be a matrix of $7 \times 7$ elements of which elements E1 to E7 extend as shown, and the other six elements orthogonal to each of E1 to E7 extend perpendicular to the paper. It should be understood that in practice slices have larger numbers of elements. If it is desired to obtain a shadowgram such as 1 looking in the direction shown at 2 then each element such as 3, of the shadowgram, can be evaluated by taking the sum of elements such as E1 of slices S1 to S5. The shadowgram will also extend by six further elements perpendicular to the paper. Thus if the absorption of a slice element is $A_E^S$ then $$A_3 = A_{E1}^{S1} + A_{E1}^{S2} + A_{E1}^{S3} + A_{E1}^{S4} + A_{E1}^{S5}$$

Figure 1:
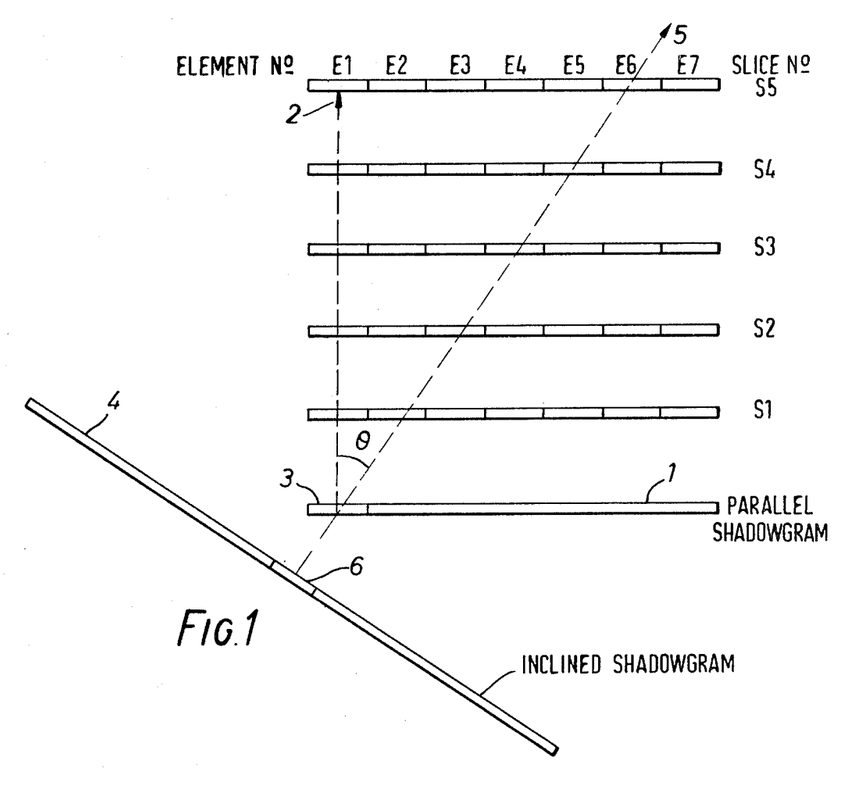
FIG. 1 illustrates the nature of a required shadowgram in terms of CAT cross-sections for a body.

Similarly a shadowgram 4 looking in the direction 5 inclined at angle $\theta$ to direction 2 will have an absorption for an element 6 given by $$A_6 = A_{E2}^{S1} + A_{E3}^{S2} + A_{E4}^{S3} + A_{E5}^{S4} + A_{E6}^{S5}$$

The total absorption for each shadowgram element may be divided by the total number of CAT elements used, to restrict the total dynamic range.

If the chosen direction of viewing for the shadowgram is such that a typical viewing line does not pass through corresponding points of the elements in all the slices then the elements contributions have to be weighted in proportion to their distances from the line for calculating the total absorption. This technique is well known and is used in the calculation of a CAT slice from edge readings for example as in British Pat. No. 1,283,915. Such weighting will only be necessary when the spatial resolution at right angles to the CAT slice planes becomes comparable to the resolution within the planes. In a typical embodiment however it is acceptable to take, in every slice, the absorption for that element whose center is nearest to the viewing line.

It may be noted that a shadowgram constructed as described hereinbefore appears to become increasingly transparent with increasing number of slices. This is quite different to the effect of superimposing film transparencies where the picture continues to become denser as more slices are added.

A practical implementation of such a display processes data from, say, eight tomographic slices. A typical slice consists of 89,600 elements (320×280), so that eight slices contain 716,800 elements. An eight-bit grey scale is associated with each element giving a total of 5.7 M bits of information to be handled.

Data for the eight (or more) slices are provided by the X-ray apparatus and are stored in a video disc recorder such as that described in the aforementioned U.S. Pat. No. 4,029,948 and U.S. Pat. No. 4,097,175. A suitable system is shown in block diagrammatic form in FIG. 2.

Figure 2:
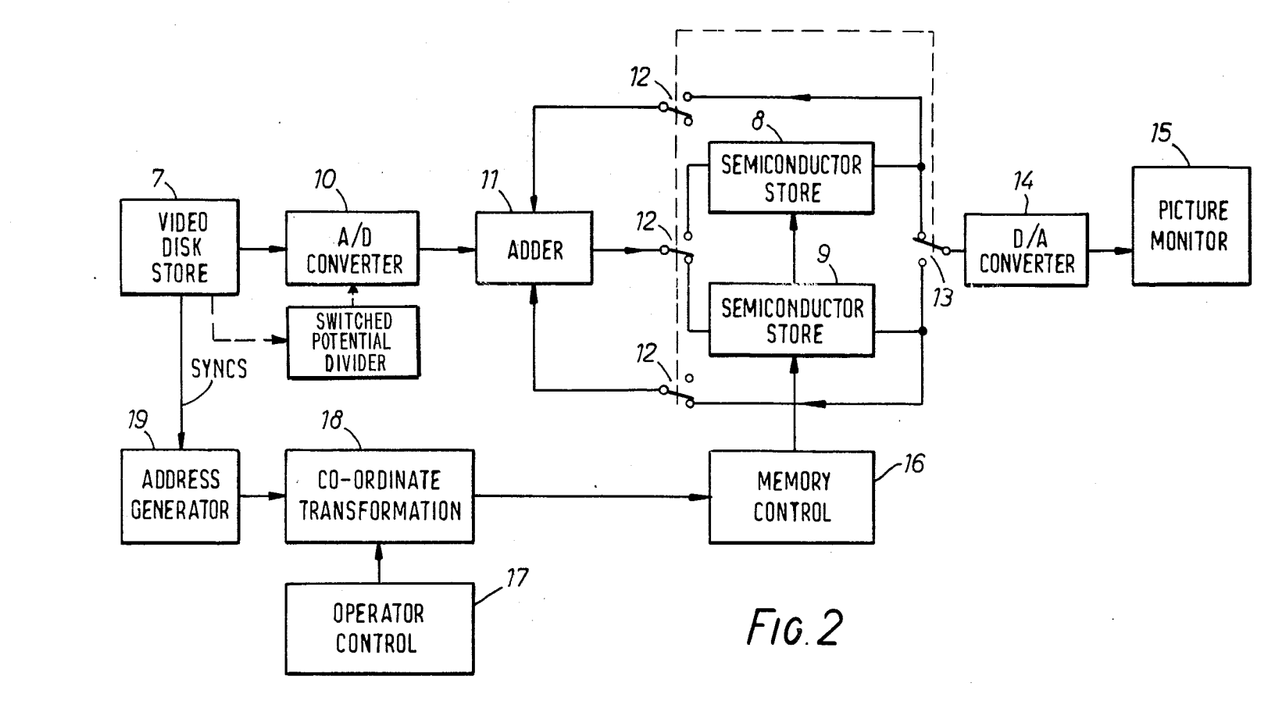
FIG. 2 shows in block diagrammatic form a circuit for implementing the invention.

A video disc recorder 7 provides data to two semiconductor stores 8 and 9 via an analogue to digital (A/D) converter 10 and an adder 11. Stores 8 and 9 are provided with recirculating paths via switches 12 and the outputs of one store or the other can be fed via a switch 13 through a digital to analogue (D/A) converter 14 to a display monitor 15. The arrangement is such that, when one store is providing data for display, the other is being up-dated with new data from disc store 7. The data for one slice are read into store at appropriate locations. The data for further slices are then arranged to overlie previous data in a manner which gives the required shadowgram.

Towards the edges of the shadowgram the sum will be far less than the full eight slices. The data may be normalized to the number of elements summed to overcome this. Usually, however, this effect will only be for unimportant data at the picture edge and can be ignored. A similar error is given by shadowgrams which do not pass through all eight slices and are sums of less than eight elements. This effects all shadowgram elements. Normalization can also be used for this case. Normalization can be achieved by a switched potential divider before converter 10. Alternatively it may be effected in stores 8, 9. Provided stores 8, 9 have sufficient storage depth, windowing prior to display gives an effect that reduces the need for normalization.

For summing the slice data a memory control 16 causes the data to be read out from appropriate locations of store 8 or 9 to be recirculated and added to the incoming data at 11. The required angle $\theta$ is input by an operator at a control unit 17. This causes a transformation on addresses for the incoming data from an address selector 19 to provide unit 16 with proper addresses from which to read out existing data and replace the data summed at 11.

Co-ordinate transformation has previously been described for computer displays for rotation of three-dimensional display images and such techniques could be adapted to the present purpose. However there will be described in greater detail a co-ordinate transformation particularly applicable to the cross-section to shadowgram progressing of this invention.

Figure 3:
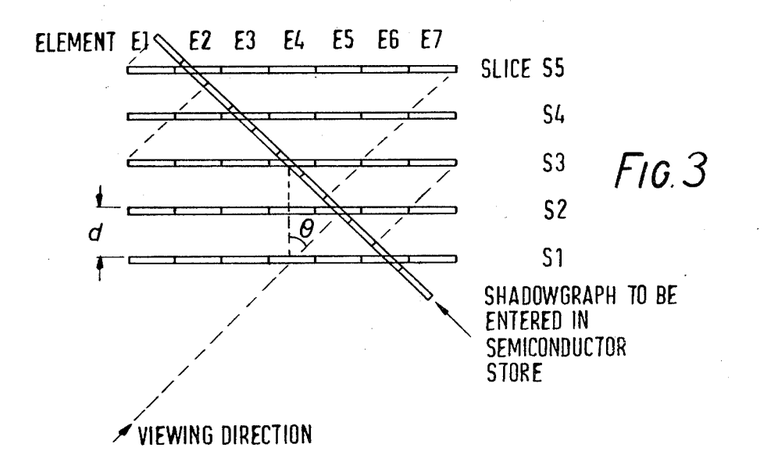
FIG. 3 illustrates the relationship of dimensions in the CAT cross-sections.
Figure 4:
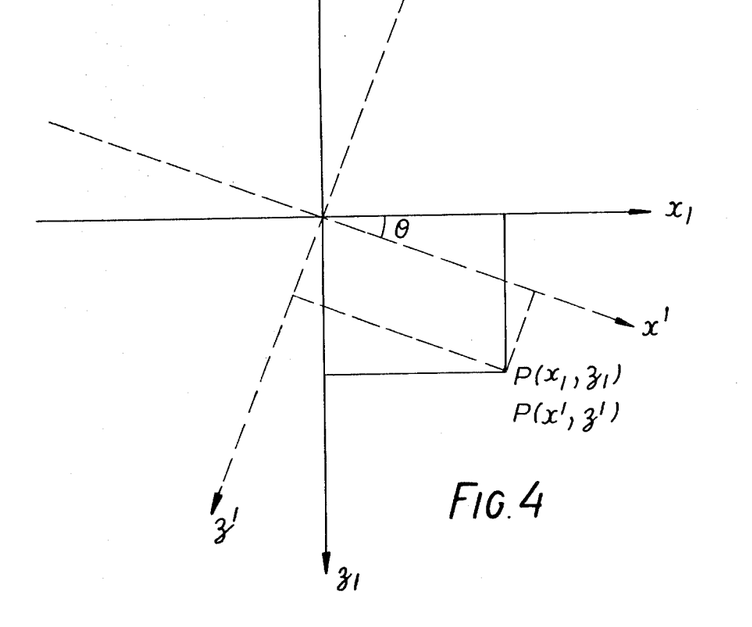
FIG. 4 and 5 illustrates the nature of the required co-ordinate transformation.

The form of co-ordinate transformation required can be seen with respect to FIG. 3 for the five slices of FIG. 1. Considering slice S3 it can be seen that this slice, and each element of it, is effectively shortened by a factor Cos $\theta$ in projection on the plane of the required shadowgram. Other slices, in addition to shortening by the factor Cos $\theta$ also suffer shifts. For example all addresses for slice S1 are shifted to the right by 2d sine $\theta$. The required co-ordinate transformation must then achieve the same shortening and shift. The situation can be considered in more general terms as shown in FIG. 4, where co-ordinates x', z' of a point are found from known co-ordinates $x_1$, $z_1$. Co-ordinate $y_1$ is perpendicular to the paper as in FIGS. 1 and 3.

Assuming $\theta$ to be positive as shown $x' = x_1 \cos\theta + z_1 \sin\theta$ $z' = z_1 \cos\theta - x_1 \sin\theta$ and $y' = y_1$ The process of updating is, on this basis, analysed into a sequence of distinct steps as follows:
(1) The address within a slice is generated (this is effectively $x_1$ of FIG. 4).
(2) This address and the slice number ($z_1$ of FIG. 4) in conjunction with $\theta$ are used to compute the new address for the semiconductor store (x' of FIG. 4)
(3) The information contained in the newly computed address is read out, added to the information from the slice and written back in. In the case of the first slice in an updating sequence, any existing information is discarded.
(4) When the last slice has been written in, the semiconductor store is switched to the display while the second store is switched to the input for updating.

The description so far has been limited to altering the viewing angle by rotating the slice array about a vertical (y) axis through the center of the array. Rotation about a horizontal (x) axis through the center of the array and parallel to the cross-section planes is equally possible and gives the impression of "tumbling". Rotation about a horizontal axis through the center of the array perpendicular to the tomogram planes is possible but the same effect can be achieved by rotation of the display or even by head movement on the part of a viewer.

Figure 5:
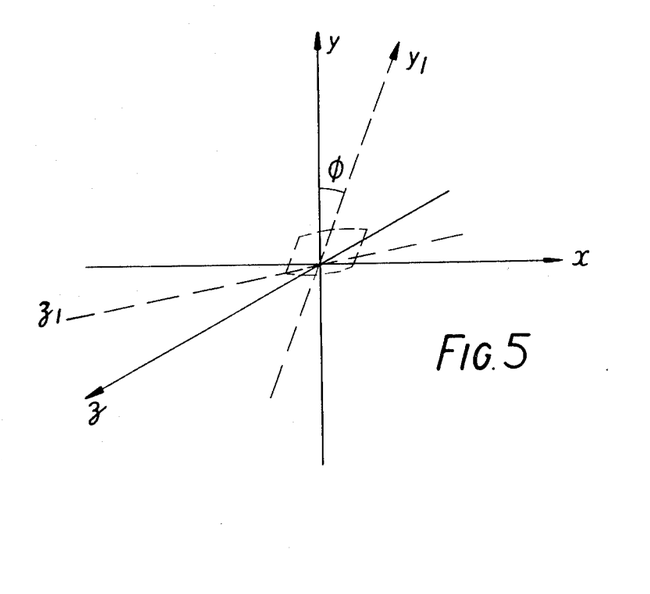

FIG. 5 shows in three dimensional view the co-ordinate transformation for rotation $\phi$ about the x-axis from x,y,z, to $x_1$, $y_1$, $z_1$, Thus $x_1 = x$ $y_1 = y \cos\phi - z \sin\phi$ and $z_1 = z \cos\phi + y \sin\phi$.

Now assuming this $x_1$, $y_1$, $z_1$, to be the pre-transformation co-ordinates of FIG. 4 the total axis rotation from x,y,z to x', y', z', can be given as $x' = x \cos\theta + z \sin\theta \cos\phi + y \sin\theta \sin\phi$ $y' = y \cos\phi - z \sin\phi$ and $z' = z \cos\theta \cos\phi + y \cos\theta \sin\phi - x \sin\phi$ In this transformation x', y' define the viewing plane for the desired shadowgram x' being defined as the line scan direction for the display and y' the field scan direction. The z' axis defines the direction of viewing and therefore does not require transformation.

FIGS. 6 to 10 show in more detail some of the circuit blocks of FIG. 2. For the purposes of these a CAT slice consisting of a square array of 256×256 picture elements is assumed for eight such slices in all. These parameters may, of course, be changed if desired.

Figure 6:
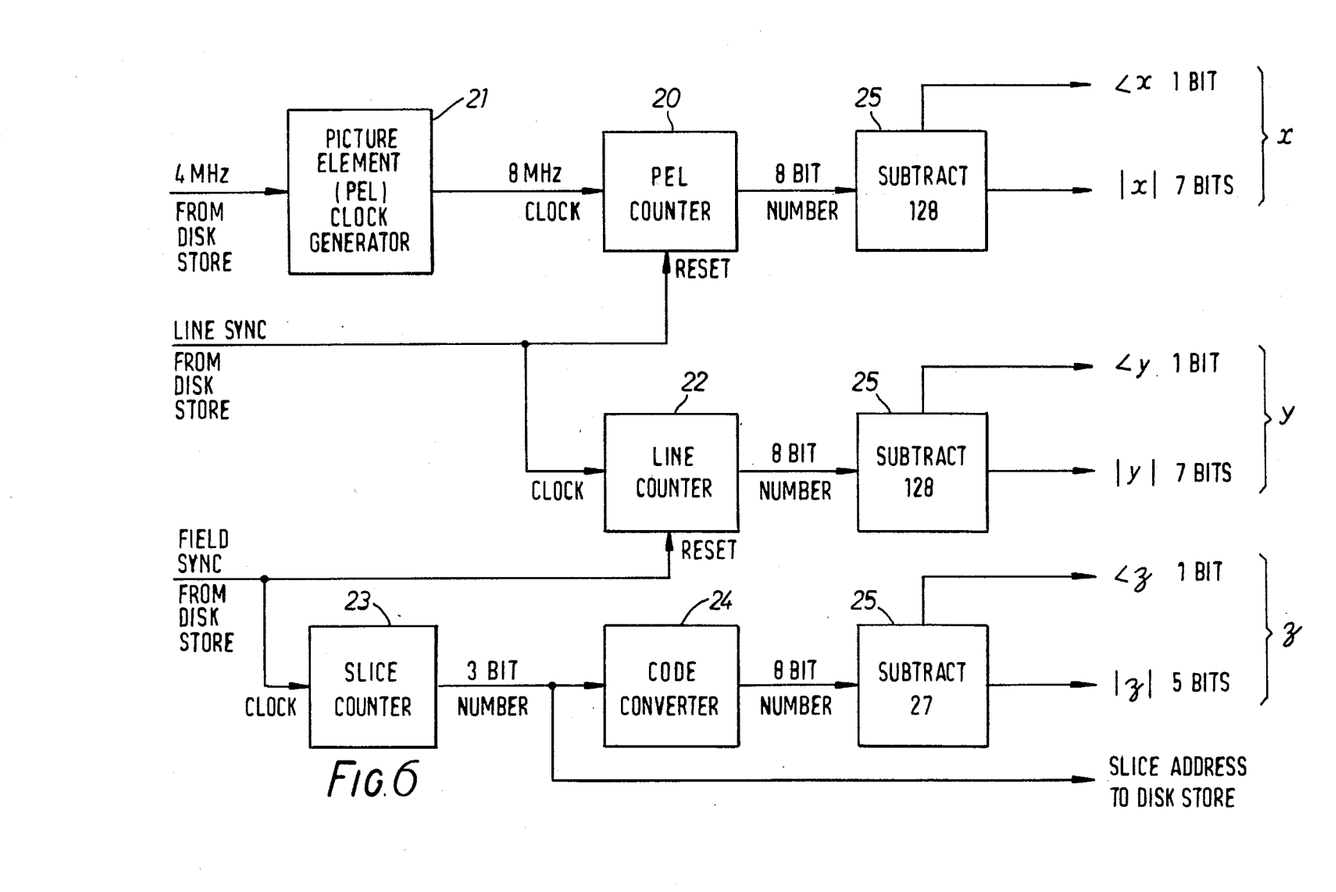
FIG. 6 shows an address generator for the circuit of FIG. 2.

FIG. 6 illustrates the address generator 19 which generates x, y, and z co-ordinates by counting: at 20, picture elements, (PEL's) as indicated by a clock generator 21; at 22, lines using the disc store synchronization and, at 23, slices using the disc store field synchronization. Code convertor 24 in the z co-ordinate generator changes the slice number into a distance in units of one PEL, assuming, in this example, a slice spacing of six PEL's. Thus eight slices occupy a distance equivalent to forty two PEL's so that z is a five bit number, plus sign. Subtractor 25 subtracts predetermined numbers to properly dimension the co-ordinates.

Figure 7:
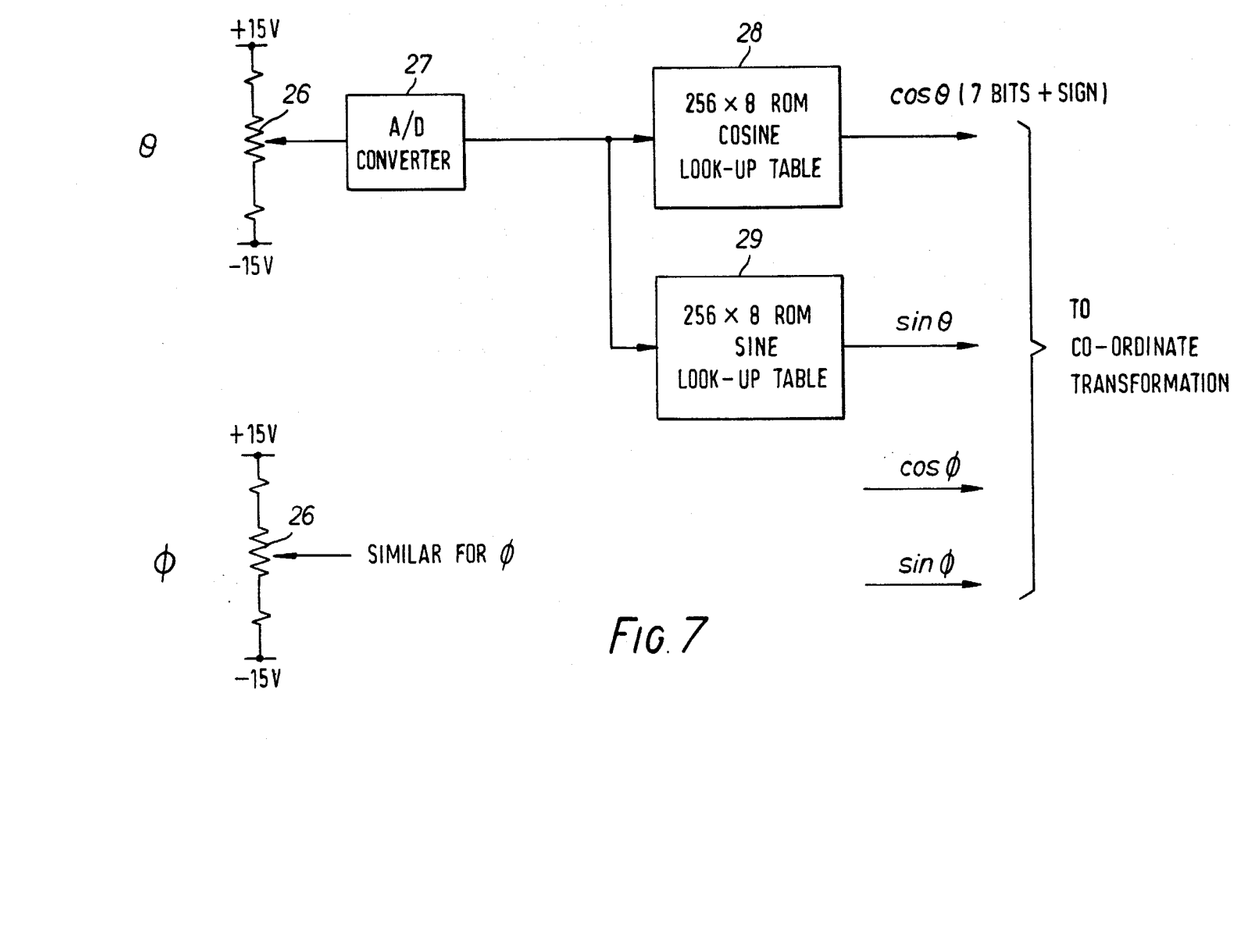
FIG. 7 shows in simplified form an operator control unit.

FIG. 7 shows in simplified form the generator of $\theta$ (and $\phi$) in operator control unit 17. Potentiometers 26 generate the variables operating, via A/D converters such as 27, look up tables 28 and 29 for cosine and sine respectively. Alternatively the potentiometers themselves can be arranged to provide the desired functions.

Figure 8:
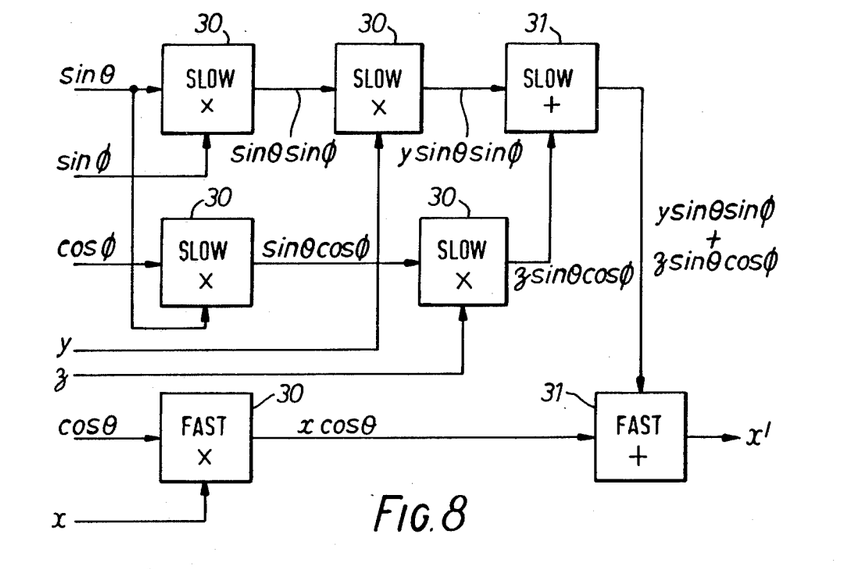
FIG. 8 shows one circuit for co-ordinate transformation.
Figure 9:
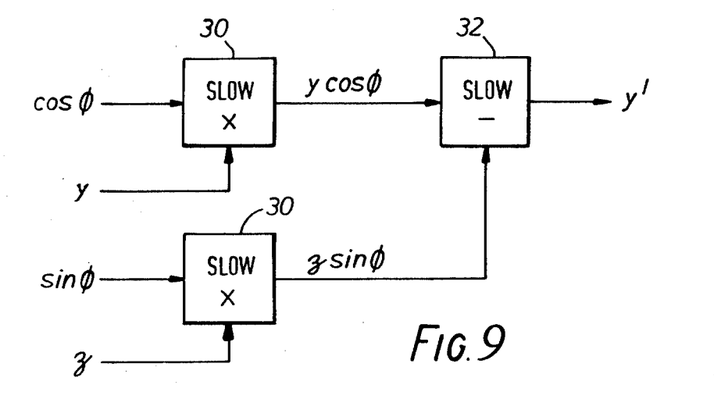
FIG. 9 shows another circuit for co-ordinate transformation.

FIGS. 8 and 9 illustrate possible arrangements for co-ordinate transformation for x' and y' respectively using multipliers 30, adders 31 and subtractors 32. The distinction between slow and fast units allows an efficient operation using low cost units where possible but is not fundamental to the operation of the circuits.

Figure 10:
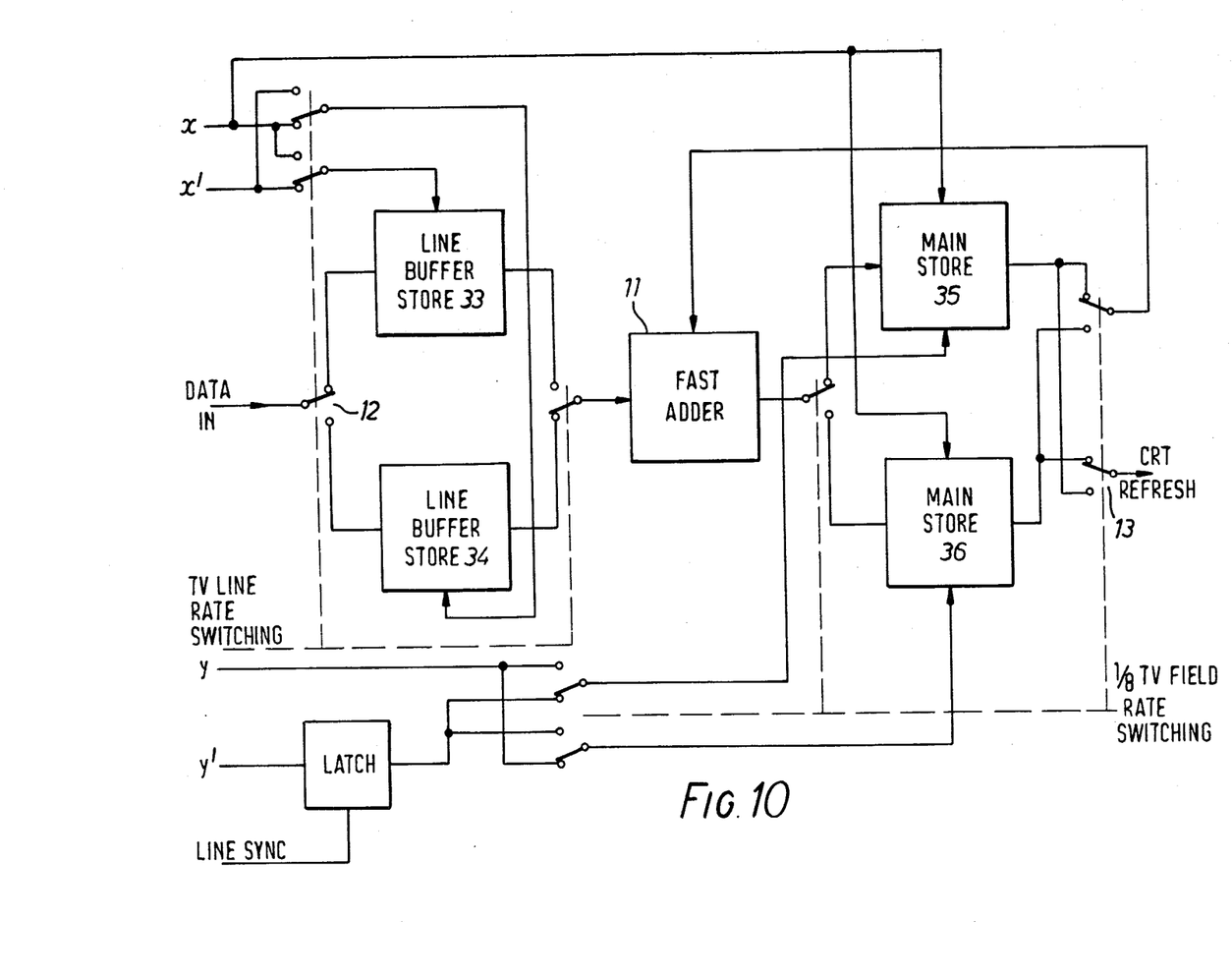
FIG. 10 shows in more detail a possible organization of the semiconductor stores of FIG. 2.

FIG. 10 shows in more detail a possible organization of semiconductor stores 8 and 9. The incoming data is for CAT cross-sections having co-ordinates in x and y. The data is first transformed from x to x' in line buffer stores 33 and 34 which are random access stores each holding one line of the incoming data. The data can thus be applied to or withdrawn from any location on the line according to the address supplied to the store simultaneously with the signal. The incoming data are of course in sequence of x as supplied by the video disc store 7. They are however read into x' locations as determined by the x' addresses supplied by co-ordinate transformation unit 18, as discussed hereinbefore. Thus, in the figure, buffer store 33 receives the incoming data and x' addresses. When this is done the data may be read out in response to the x addresses direct from the disc store 7 (or the circuits controlling that store) and their sequence will be the co-ordinate transformed one. Thus in FIG. 10 buffer store 34 is transmitting data to the next part of the circuit in response to the x addresses.

The y to y' transformation is carried out in main stores 35 and 36 which can be slow random access memories (RAMs) programmed to operate in sequential manner to accept each line from a buffer store in sequence (in response to the x addresses which, since that co-ordinate has been transformed, may be used from this point). In the practical arrangement adder 11 is situated immediately before stores 35 and 36 to recirculate the already-stored data, not prior to all storage as in the simplified FIG. 2. The y transformation is achieved in a manner similar to the x transformation. Although the data are applied in sequence within each line, they are put to their appropriate y locations not in the sequence in which they arrive but "randomly" i.e. as determined by the y' addresses from transformation unit 18. Thus in FIG. 10, main store receives a lines from the buffer stores and "randomly" stores them in response to y' (and x) addresses. Once stored, and therefore transformed, the data can be read out to the CRT in display sequence as determined by the x and y addresses. Thus in FIG. 10 main store 36 is supplying a set of totally transformed pictures summed to a shadowgram to the CRT in response to x and y addresses.

In this practical embodiment the switching from one store to the other for output or updating, is at one eighth of the T.V. field rate although that rate can be varied. Furthermore a latch is provided to properly relate the y' addresses to the line sync of the display which must be maintained if the display is to be properly controlled. The line buffer stores are, of course, switched at the T.V. line rate.

Windowing in real time of the shadowgraph display would be possible as described in the aforementioned British Pat. No. 1,283,915 since the signal is available in digital form. However windowing is restricted in practice because of the limited dynamic range of the disc recorder. By using two tracks on the disc for each slice, the full dynamic range can be stored. Two A/D converters are then necessary and the semi-conductor stores have to be bigger. Additional stations on the disc recorder may be used to supply data for display allowing the elimination of one of the semi-conductor stores, or to halving the updating time.

Although the invention is primarily intended for the processing of cross-sectional X-ray data from CAT apparatus to give X-ray shadowgrams, it will be realised that it may have wider application. In general it may be used to process any data derived as two dimensional representations of a quantity in cross-sections of a patient, to provide shadowgram equivalent pictures of the distribution of the relevant quantity. That is to say pictures which represent the sum total of the quantity in the direction of viewing.

What I claim is:

1. An apparatus for processing, for display, values of a quantity, for example, X-ray absortion, measured in a region of the body of a patient, the apparatus including: storage means for receiving data signals representing the measured values for respective elemental areas of a plurality of cross-sectional slices of the body, each data signal being identified by the co-ordinates of the respective element in the body according to a first co-ordinate system; transformation means coupled with said storage means for transforming the co-ordinates for the data signals received by said storage means to the co-ordinates for the same elements according to a second co-ordinate system, in two dimensions orthogonal to a selected direction in the body; and means coupled with said storage means for summing, for the plurality of slices, data signals received by said storage means which are identified by substantially the same co-ordinates in the second system, to thereby provide a representation which is the sum of the individual slices viewed in the selected direction.

2. An apparatus according to claim 1 including second storage means in which the data signals are stored at locations corresponding to the second co-ordinates of the respective elements.

3. An apparatus according to claim 2 in which the means for summing include means for withdrawing from the second storage means data signals already stored in a location corresponding to the second co-ordinates of a new data signal, means for adding the signals withdrawn to the new data signal and means for applying the resulting sum to the second storage means in the same location.

4. An apparatus according to claim 2 including buffer storage means, means for applying the data signals to the buffer storage means in a sequence corresponding to the respective first co-ordinates, means for deriving the data signals therefrom in a sequence corresponding to one of the respective second co-ordinates and means for applying the data to the second storage means at locations corresponding to both of the respective second co-ordinates.

5. An apparatus according to claim 1 adapted to receive the data signals for the respective slices in the form of television standard signals, including an address generator for generating addresses for the data signals, in the first co-ordinate system using the television synchronization signals.

6. An apparatus according to claim 1 including means for normalizing the summed data signals according to the number of individual data signals contributing thereto.

7. An apparatus for processing, for display, values of a quantity, for example X-ray absorption, measured in a region of the body of a patient, the apparatus including: storage means for receiving data signals, representing the measured values for respective elemental areas of a plurality of cross-sectional slices of the body, and for storing each data signal at a location corresponding to the respective elemental area and identified according to an orthogonal co-ordinate system representing position in the region; further storage means for storing further data signals in locations, each of which corresponds to respective co-ordinates of a further, two-dimensional, co-ordinate system orthogonal to a selected direction in the body; transformation means for transforming the first mentioned co-ordinates for each of the elemental areas into said further co-ordinates; means for summing for the plurality of slices, measured values for elements in the different slices having the same further co-ordinates to form said further data signals; and means for entering the summed values into the further storage means at the locations corresponding to their further co-ordinates to provide a representation which is a sum of the individual slices viewed in the selected direction.

8. An apparatus for display of data, provided by a medical radiographic apparatus, representing distributions of X-ray absorption in each of a plurality of substantially parallel cross-sectional slices of the body of a patient, the apparatus including: means for storing the data for individual elements of each of the slices at locations corresponding to their position in the body; means for summing data signals from different slices for elements which lie along the same line in the body in a selected direction, to provide a shadowgram picture for the body, viewed in the selected direction; and means for displaying the shadowgram picture so derived.

9. A method of processing, for display, data signals representing values of a quantity, for example X-ray absorption, in elements of each of a plurality of cross-sectional slices of the body of a patient, the method including summing data signals for all elements which lie along substantially the same line through the body in a selected direction to provide elements of a representation of the body, in terms of the measured quantity, which is a superimposition of the individual slices viewed in the selected direction.

10. A method according to claim 9, in which the data signals are originally indentified according to a three dimensional co-ordinate system in the body, including transforming the co-ordinates for the data signals to a two dimensional system orthogonal to the selected direction and summing all data signals which have the same co-ordinates.

11. A method according to claim 10 including normalizing each summed data signal according to the number of data signals forming the sum.

12. A method according to claim 9 in which the data signals summed are those for elements which lie within a predetermined distance of a line in the selected direction and their contributions to the sum are weighted according to the distance of their center from the line.

* * * * *